(12) United States Patent
Droste et al.

(10) Patent No.: US 10,242,542 B2
(45) Date of Patent: Mar. 26, 2019

(54) ALARM PANE ARRANGEMENT

(71) Applicant: SAINT-GOBAIN GLASS FRANCE, Courbevoie (FR)

(72) Inventors: Stefan Droste, Herzogenrath (DE); Guillaume Francois, Aachen (DE); Christian Effertz, Aachen (DE)

(73) Assignee: SAINT-GOBAIN GLASS FRANCE, Courbevoie (FR)

( * ) Notice: Subject to any disclaimer, the term of this patent is extended or adjusted under 35 U.S.C. 154(b) by 0 days.

(21) Appl. No.: 15/741,258

(22) PCT Filed: Nov. 19, 2016

(86) PCT No.: PCT/EP2016/078214
§ 371 (c)(1),
(2) Date: Dec. 30, 2017

(87) PCT Pub. No.: WO2017/085302
PCT Pub. Date: May 26, 2017

(65) Prior Publication Data
US 2018/0197388 A1 Jul. 12, 2018

(30) Foreign Application Priority Data
Nov. 19, 2015 (EP) .................................... 15195333

(51) Int. Cl.
*G08B 13/00* (2006.01)
*G08B 13/04* (2006.01)
*G01N 27/22* (2006.01)

(52) U.S. Cl.
CPC ............. *G08B 13/04* (2013.01); *G01N 27/22* (2013.01)

(58) Field of Classification Search
CPC .................... B32B 17/10036; B32B 17/10174
(Continued)

(56) References Cited

U.S. PATENT DOCUMENTS

| 4,092,636 A | 5/1978 | Shepherd, Jr. |
| 4,684,929 A | 8/1987 | Edwards et al. |

(Continued)

FOREIGN PATENT DOCUMENTS

| CN | 203224957 U | 10/2013 |
| CN | 203232520 U | 10/2013 |

(Continued)

OTHER PUBLICATIONS

International Search Report for International Application No. PCT/EP2016/078214 filed Nov. 19, 2016 on behalf of Saint-Gobain Glass France, dated Mar. 14, 2017. 7 pages. (German + English Translation).

(Continued)

*Primary Examiner* — Fabricio R Murillo Garcia
(74) *Attorney, Agent, or Firm* — Steinfl + Bruno LLP

(57) ABSTRACT

The present invention relates to an alarm pane arrangement having: at least one first pane which is composed of tempered glass, having an outside surface and an inside surface, at least one transparent, electrically conductive coating which is arranged on the inside surface of the first pane, a sensor unit with a capacitive sensor which is capacitively coupled to the transparent, electrically conductive coating, where the sensor unit outputs an alarm signal in the event of deviations in a measurement signal of the capacitive sensor from a comparison value, where the capacitive sensor contains i) precisely one measuring electrode or ii) a measuring electrode and a reference ground electrode or iii) a measuring electrode, a reference ground electrode and at least one compensation electrode, and where the measuring electrode is DC-isolated from the transparent, electrically conductive coating.

24 Claims, 7 Drawing Sheets

Figure 1A:
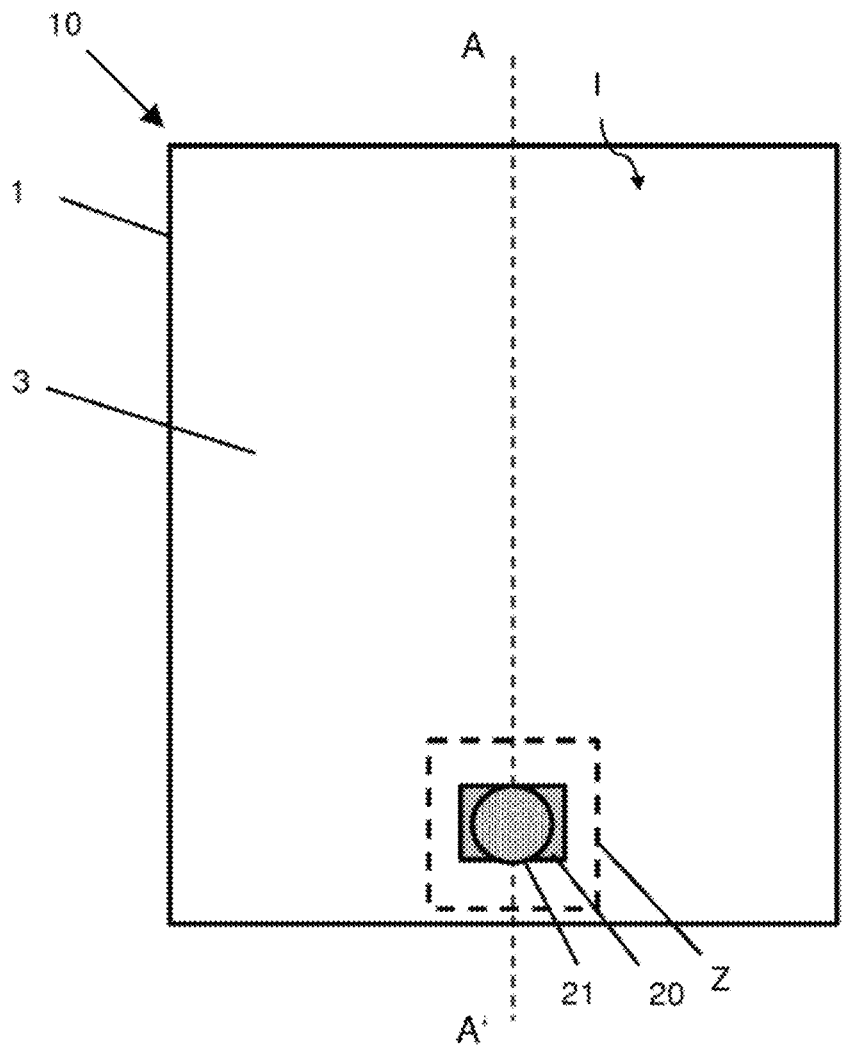

(58) Field of Classification Search
USPC .......................................................... 340/550
See application file for complete search history.

(56) References Cited

U.S. PATENT DOCUMENTS

| | | | | |
|---|---|---|---|---|
| 2002/0045037 | A1* | 4/2002 | Boire ...................... | C03C 17/36 |
| | | | | 428/216 |
| 2009/0134024 | A1* | 5/2009 | Neel ................ | G01N 33/48771 |
| | | | | 204/406 |
| 2010/0090597 | A1* | 4/2010 | Werners ............ | B32B 17/10036 |
| | | | | 313/512 |
| 2011/0139756 | A1 | 6/2011 | Raible et al. | |
| 2012/0080421 | A1* | 4/2012 | Macher ................... | H05B 3/84 |
| | | | | 219/522 |

FOREIGN PATENT DOCUMENTS

| | | |
|---|---|---|
| DE | 4300350 A1 | 7/1994 |
| DE | 4327664 C1 | 11/1994 |
| DE | 19754295 A1 | 6/1999 |
| DE | 19913766 A1 | 4/2000 |
| DE | 19860872 A1 | 7/2000 |
| EP | 0058348 A2 | 8/1982 |
| EP | 0847965 B1 | 10/2004 |
| EP | 2139049 A1 | 12/2009 |
| EP | 2200097 A1 | 6/2010 |
| GB | 2181586 A | 4/1987 |
| JP | 2003-141649 A | 5/2003 |
| JP | 2005-326251 A | 11/2005 |
| WO | 01/22378 A1 | 3/2001 |
| WO | 2012/031912 A1 | 3/2012 |

OTHER PUBLICATIONS

Written Opinion for International Application No. PCT/EP2016/078214 filed on Nov. 19, 2016 on behalf of Saint-Gobain Glass France, dated Mar. 14, 2017. 14 pages. (English translation + German original).

International Search Report for International Application No. PCT/EP2016/078215 filed on Nov. 19, 2016 on behalf of Saint-Gobain Glass France, dated Mar. 24, 2017. 7 pages. (English translation + German original).

Written Opinion for International Application No. PCT/EP2016/078215 filed on Nov. 19, 2016 on behalf of Saint-Gobain Glass France, dated Mar. 24, 2017, 15 pages. (English translation + German original).

International Search Report for International Application No. PCT/EP2017/068843 filed Jul. 26, 2017on behalf of Saint-Gobain Glass France. dated Oct. 26, 2017. 7 pages. (English Translation + German Original).

International Search Report for International Application No. PCT/EP2017/068844 filed Jul. 26, 2017 on behalf of Saint-Gobain Glass France. dated Oct. 26, 2017. 6 pages. (English Translation + German Original).

Korean Office Action for Korean Application No. 10-2018-7004591 filed Feb. 2, 2018 on behalf of Saint-Gobain Glass France. dated Oct. 24, 2018. 12 pages (English Translation Only).

Korean Office Action for Korean Application No. 10-2018-7004593 filed Feb. 14, 2018 on behalf of Saint-Gobain Glass France. dated Oct. 25, 2018. 12 pages (English Translation Only).

* cited by examiner

ALARM PANE ARRANGEMENT

CROSS REFERENCE TO RELATED APPLICATIONS

The present application is the U.S. national stage of International Patent Application PCT/EP2016/078214 filed internationally on Nov. 19, 2016, which, in turn, claims priority to European Patent Application No. 15195333.8 filed on Nov. 19, 2015.

The invention relates to an alarm pane arrangement, in particular for an insulating glazing, with a transparent, electrically conductive coating and a capacitive sensor. The invention further relates to a method for operating the alarm pane arrangement.

To detect the breakage of a pane, for example, in the event of a break-in or other damage, so-called "alarm panes" are used. These alarm panes are usually a component of an insulating glazing unit or a multiple glazing unit. As a rule, at least one pane is made of toughened single-pane safety glass (SPSG). In the event of damage, the toughened pane breaks, over its entire area, into small fragments.

A conductor loop, whose resistance is measured by an evaluation electronic system, such as is known, for example, from EP 0 058 348 A2, is customarily arranged on alarm panes. When the alarm pane breaks, the conductor loop is also destroyed and a change in resistance is measured. The evaluation electronic system outputs an alarm signal in this case. Such conductor loops are not very attractive visually, are expensive to produce and difficult to contact.

DE 197 54 295 A1 shows an arrangement in which two measuring electrodes spaced at a distance from one another are galvanically connected to an electrically conductive layer.

The object of the present invention now consists in providing an improved alarm pane arrangement that is simple and economical to produce and is less visible optically. In addition, the alarm pane arrangement according to the invention is suitable to be produced in a retrofitting process with already existing panes.

The object of the present invention is accomplished according to the invention by an alarm pane arrangement in accordance with the disclosure. Preferred embodiments are also disclosed.

The alarm pane arrangement according to the invention comprises at least:
- at least one first pane, made of toughened glass, having an outside surface (I) and an inside surface (II),
- at least one transparent, electrically conductive coating, arranged on the inside surface (II) of the first pane, and
- a sensor unit with a capacitive sensor, which is capacitively coupled to the transparent, electrically conductive coating, wherein the sensor unit outputs an alarm signal in the event of deviations in a measurement signal of the capacitive sensor from a comparison value.

The invention is based on the knowledge that many panes, and, in particular, insulating glass panes already have transparent coatings with good electrical conductivity. These transparent, electrically conductive coatings have diverse purposes: for example, reflecting infrared radiation or low-E properties. The alarm pane arrangement according to the invention includes a sensor unit that monitors the integrity of the pane with a sensor without contact and outputs an alarm signal in the event of breakage of the pane. Complex contacting of the transparent, electrically conductive coating is eliminated by the contact-free monitoring. Such contacts are customarily soldered and highly susceptible to aging since the contact resistance at the solder joint is altered by aging processes. This does not present a problem with capacitive monitoring since the direct electrical contact of the transparent, electrically conductive coating is eliminated. Since an already present transparent, electrically conductive coating is used, a separate production step, for example, for printing an electrical conductor loop, is eliminated. The transparent, electrically conductive coating is hardly visible optically and is, consequently, very aesthetic. It can, for example, also have antireflective properties and further improve visibility through the pane. All of this was unexpected and surprising for the inventors.

An alarm pane arrangement according to the invention includes at least one first pane having an outside surface (I) and an inside surface (II). The first pane usually serves for separating an exterior space from an interior space, for example, of a building, of a display case, or of a vehicle. In this case, the outside surface (I) can face the outside, i.e., outward; and the inside surface (II), the inside, i.e., inward.

In the case of a use of the alarm pane arrangement for protection of an interior space against theft or damage, the outside surface (I) would be the so-called "exposed side" from which intrusion usually occurs. In this case, the inside surface (II) with the capacitive sensor and the sensor unit would be protected against tampering, since they would not be accessible until after breakage and removal of the first pane.

In the case of the alarm pane arrangement for breakage monitoring, for example, in a vehicle such as a train or an aircraft, the inside surface (II) can also be exposed to potential attacks, for example, destruction with an emergency hammer in the event of danger. In this case, deliberate tampering with the sensor unit is not likely.

Of course, the outside surface (I) of the first pane can also have a further coating, for example, a further transparent, electrically conductive coating. In an advantageous embodiment of the alarm pane arrangement according to the invention, the sensitivity of the sensor can be selected such that only the integrity of the transparent, electrically conductive coating on the inside surface (II) of the first pane is monitored, or, in addition, the integrity of the other transparent, electrically conductive coating on the outside surface (I) of the first pane is also monitored.

In an advantageous embodiment of an alarm pane arrangement according to the invention, the transparent, electrically conductive coating is bonded to the first pane such that in the event of breakage of the first pane, the transparent, electrically conductive coating is damaged. For this, the transparent, electrically conductive coating is preferably deposited directly on the inside surface (II) of the first pane, particularly preferably as a thin-film stack. Particularly suitable methods for this are cathodic sputtering (sputtering, in particular magnetron sputtering), chemical vapor deposition (CVD), and/or thermal evaporation. This is particularly advantageous for enabling reliable detection of breakage of the first pane.

In an advantageous embodiment of the alarm pane arrangement according to the invention, the capacitive sensor includes at least one electrode, preferably
i) precisely one measuring electrode or
ii) a measuring electrode and a reference ground electrode, in particular precisely one measuring electrode and precisely one reference ground electrode, or
iii) a measuring electrode, a reference ground electrode, and at least one compensation electrode, which is arranged between the measuring electrode and the reference ground electrode, in particular precisely one measuring electrode, precisely one reference ground electrode, and at least one compensation electrode, which is arranged between the measuring electrode and the reference ground electrode.

In an advantageous embodiment of the alarm pane arrangement according to the invention, the measuring electrode is galvanically isolated from the transparent, electrically conductive coating.

In an advantageous embodiment of the alarm pane arrangement according to the invention, the distance d between the measuring electrode and the transparent, electrically conductive coating is from 0.1 mm to 20 mm, preferably from 0.2 mm to 10 mm, and in particular from 0.5 mm to 5 mm.

The first pane is made of toughened glass. In an advantageous embodiment of the first pane, it is toughened such that in the event of breakage of the first pane, the fragments are smaller than a detection region of the capacitive sensor. If the fragments are smaller, for example, because they have a smaller area than the detection region or a smaller maximum diameter than the detection region, it is guaranteed that at least one break line lies within the detection region of the sensor, enabling reliable detection of breakage of the first pane.

In an advantageous embodiment of the alarm pane arrangement according to the invention, the sensor unit is arranged on the inside of the first pane, i.e., on the side that is defined by the inside surface (II) of the first pane. This is particularly advantageous for protecting the sensor unit against damage and tampering attempts from the exposed side, i.e., from the side of the first pane that is defined by the outside surface (I).

The capacitive sensor functions, in principle, like an open capacitor, between whose measuring electrode and whose reference ground electrode, an electric (AC) field is established. The electric field interacts with the transparent, electrically conductive coating, and a total capacitance of the arrangement can be measured.

In an advantageous embodiment of the alarm pane arrangement according to the invention, the sensor unit includes a sensor electronic system, preferably with at least the following components: an oscillator, which applies an alternating electrical voltage to the measuring electrode and, optionally, to the reference ground electrode; a demodulator, which outputs, based on the measured AC voltage signal, a capacitance measurement signal proportional thereto; a comparator, which compares the capacitance measurement signal with a comparison value or a threshold value; and a power amplifier, which, optionally, outputs an output signal adjusted to customary signal voltage levels.

In an advantageous embodiment of the alarm pane arrangement according to the invention, the sensor unit has a transmitter unit, preferably a radio transmitter unit with a radio signal whose frequency is in the range from 100 kHz to 100 GHz. The radio transmitter unit is particularly preferably a Bluetooth transmitter or a WLAN transmitter. Alternatively, the transmitter unit can also be an infrared transmitter. The transmitter unit serves for communication with a receiver and, in particular, for transmitting an alarm signal when the sensor unit detects breakage of the pane. The integration of a transmitter unit has the particular advantage that the sensor requires no external leads for transmission of the alarm signal, and thus a very simple, economical, and location-independent installation is enabled. Moreover, a possibility of tampering with the sensor unit is eliminated, by which means security is increased. This is particularly advantageous for the use or retrofitting of the sensor unit in an insulating glazing unit, which is customarily sealed to the outside. Of course, other data can also be transmitted via the transmitter unit, such as functional status of the sensor unit, battery or accumulator charge status, or other parameters that are provided by other sensors, such as temperature or pressure.

In another advantageous embodiment of the alarm pane arrangement according to the invention, the receiver communicating with the transmitter unit is arranged on the same side of the first pane as the transmitter unit and the sensor, namely, on the inner side of the first pane. This is particularly advantageous, in the event of use of the alarm pane arrangement for the protection of an interior against theft or damage, since the sensor unit, transmitter unit, and receiver are protected against damage and tampering and are only accessible after breakage of the first pane. In the case of the alarm pane arrangement for monitoring breakage, for example, in a vehicle such as a train or an aircraft, the receiver can be arranged on either side of the first pane, so long as the first pane with the transparent, electrically conductive coating or its vicinity is adequately permeable to to the signal of the transmitter.

In an advantageous embodiment of the alarm pane arrangement according to the invention, the sensor unit includes an energy supply, preferably a battery, an accumulator, a supercapacitor, a thermoelectric generator, and/or a solar cell. The sensor unit advantageously includes no leads to an external power supply, but is energy self-sufficient. Alternatively, the energy supply can also be done or supplemented by continuous or discontinuous charging via, for example, an inductive charging device. This has the special advantage that the sensor unit requires no external leads and thus a very simple, economical, and location-independent installation is enabled. Moreover, a possibility of tampering with the sensor unit is eliminated, which increases security. This is particularly advantageous for the use or the retrofitting of the sensor unit in an insulating glazing unit, which is customarily sealed to the outside.

The alarm pane arrangement according to the invention can be used as a single-pane or as part of a multipane glazing, for example, part of an insulating glazing, double insulating glazing, triple insulating glazing, fire-resistant glazing, or safety glazing with composite panes.

In an advantageous embodiment of the alarm pane arrangement according to the invention, the first pane is bonded to at least one other pane via at least one spacer, preferably a circumferential spacer completely surrounding the edge of the pane. The spacer is situated between the first pane and the other pane and is preferably fixed by adhesive bonding between the spacer and the panes. The spacer preferably comprises at least one hollow main body with at least two parallel pane-contact walls, one outer wall with a gas-tight insulating layer, and a glazing interior wall.

As a main body, all hollow body profiles known according to the prior art can be used regardless of their material composition. Mentioned here by way of example are polymeric or metallic main bodies.

Polymeric main bodies preferably contain polyethylene (PE), polycarbonates (PC), polypropylene (PP), polystyrene, polybutadiene, polynitriles, polyesters, polyurethanes, polymethyl methacrylates, polyacrylates, polyamides, polyethylene terephthalate (PET), polybutylene terephthalate (PBT), particularly preferably acrylonitrile butadiene styrene (ABS), acrylonitrile styrene acrylester (ASA), acrylonitrile butadiene styrene-polycarbonate (ABS/PC), styrene acrylonitrile (SAN), PET/PC, PBT/PC, and/or copolymers or mixtures thereof. Polymeric main bodies can optionally also contain other components, such as, for example, glass fibers. The polymeric materials used are, as a rule, gas-permeable such that if this permeability is undesirable, further measures must be taken.

Metallic main bodies are preferably made of aluminum or stainless steel and preferably have no gas permeability.

In an advantageous embodiment, the walls of the main body are gas-permeable. Regions of the main body in which such permeability is undesirable can, for example, be sealed with a gas-tight insulating layer. In particular, polymeric main bodies are used in combination with such a gas-tight insulating layer.

The main body preferably has a hollow chamber that contains a desiccant, preferably silica gel, $CaCl_2$, $Na_2SO_4$, activated carbon, silicates, bentonites, zeolites, and/or mixtures thereof, particularly preferably molecular sieves. Thus, absorption of air moisture by the desiccant is permitted and hence fogging of the panes and, in particular, of the capacitive sensor is prevented.

The outer intermediate space between the first pane, another pane, and the spacer is preferably sealed relative to the space outside the pane by at least one sealing compound. The sealing compound preferably contains organic polysulfides, silicones, RTV (room temperature vulcanizing) silicone rubber, HTV (high temperature vulcanizing) silicone rubber, peroxide vulcanizing silicone rubber, and/or addition vulcanizing silicone rubber, polyurethanes, butyl rubber, and/or polyacrylates. In an optional embodiment, additions to increase aging resistance, for example, UV stabilizers can also be included.

In an advantageous embodiment of the alarm pane arrangement according to the invention, the first pane is bonded via a spacer to a second pane and forms an insulating glass pane with double glazing.

In a particularly advantageous embodiment, the first pane is bonded via its inside surface (II) to the second pane.

In another particularly advantageous embodiment, the sensor unit is arranged in an intermediate space between the first pane and the second pane. This has the particular advantage that the sensor and the sensor unit are protected against outside influences such as moisture and dust, but are also particularly well protected against tampering and damage.

In an arrangement that includes a first pane and a second pane, the measuring electrode is advantageously not arranged precisely in the center between the panes, but nearer the first pane to be monitored, which has the transparent electrically conductive coating. Of course, in this arrangement, both panes, which can be monitored by two measuring electrodes, can also have a transparent, electrically conductive coating.

The first pane or the second pane can be bonded via another spacer to another third pane and thus form an insulating glazing pane with triple glazing.

In an advantageous embodiment of the alarm pane arrangement according to the invention, the first pane is made of flat glass, float glass, soda lime glass, quartz glass, or borosilicate glass.

The first pane is toughened, preferably in accordance with DIN 12150-1: Glass in Building—Thermally Toughened Soda Lime Single-Pane Safety Glass—Part 1: Definition and Description, particularly preferably with a surface compressive stress greater than 100 N/mm² and in particular from 100 N/mm² to 150 N/mm². Due to the toughening, the first pane shatters when damaged preferably into blunt-edged fragments having sizes of less than 1 cm².

The second, third, or further pane preferably contains glass, particularly preferably flat glass, float glass, quartz glass, borosilicate glass, soda lime glass, or clear plastics, preferably rigid clear plastics, in particular polyethylene, polypropylene, polycarbonate, polymethylmethacrylate, polystyrene, polyamide, polyester, polyvinylchloride, and/or mixtures thereof. Suitable glasses are known, for example, from EP 0 847 965 B1. The second, third, or further pane can be made of the aforementioned materials.

The thickness of the first, second, third, or further pane can vary widely and thus be ideally adapted to the requirements of the individual case. Preferably, panes with the standard thicknesses from 1.0 mm to 50 mm and preferably from 3 mm to 16 mm are used. The size of the pane can vary widely and is governed by the size of the use according to the invention.

In an advantageous embodiment of the invention, the first pane has dielectric properties and a relative permittivity number of 6 to 8 and in particular of approx. 7.

The panes can have any three-dimensional shape. Preferably, the three-dimensional shape has no shadow zones such that it can, for example, be coated by cathodic sputtering. Preferably, the panes are planar or slightly or greatly curved in one or a plurality of spatial directions. The panes can be colorless or colored.

In a preferred embodiment of the alarm pane arrangement according to the invention, the first pane is areally bonded via its outside surface (I) and at least one intermediate layer, preferably a thermoplastic intermediate layer, to a second pane to form a composite pane. The second pane can, in turn, be areally bonded via another intermediate layer to a further third pane. The second and/or the third pane preferably contains a plastic. The second and/or the third pane can be made of a plastic. Such composite panes are particularly breach-resistant against penetration from outside such that high safety classes can be obtained. The panes of the composite pane are bonded to one another by at least one intermediate layer. The intermediate layer preferably contains a thermoplastic plastic, such as polyvinyl butyral (PVB), ethylene vinyl acetate (EVA), polyurethane (PU), polyethylene terephthalate (PET), or a plurality of layers thereof, preferably with thicknesses from 0.3 mm to 0.9 mm.

In an advantageous embodiment of the alarm pane arrangement according to the invention, the transparent, electrically conductive coating is arranged on at least 70%, preferably 80% to 100%, and particularly preferably 98% to 100% of the through-vision area of the first pane. The through-vision area is the area of the first pane where vision is not prevented by the frame, spacers, or other attachment parts.

In an alternative advantageous embodiment of the alarm pane arrangement according to the invention, the transparent, electrically conductive coating is arranged on at least 50%, preferably at least 70%, particularly preferably 80% to 100%, and in particular 95% to 100% of the area of the inside surface of the first pane.

The transparent, electrically conductive coating according to the invention is transparent to electromagnetic radiation, preferably electromagnetic radiation of a wavelength from 300 to 1300 nm, in particular to visible light from 390 nm to 780 nm. The term "transparent" means that the total transmittance of the pane, in particular for visible light, is preferably >70% and in particular >75% transparent. For specific applications, a lower transmittance can also be desirable, for which "transparent" can also mean 10% to 70% light transmittance. Such applications are, for example, glazings for the protection of objects that should not be exposed to major light irradiation, for example, paintings or textiles.

The transparent, electrically conductive coating is preferably a functional coating, particularly preferably a functional coating with solar protection action. A coating with solar protection action has reflection properties in the infrared range and thus in the range of solar irradiation. Thus, a heating up of the interior of a vehicle or building as a result of sunlight is reduced. Such coatings are known to the person skilled in the art and typically contain at least one metal, in particular silver or a silver-containing alloy. The transparent, electrically conductive coating can include a sequence of multiple individual layers, in particular at least one metallic layer and dielectric layers that contain, for example, at least one metal oxide. The metal oxide preferably includes zinc oxide, tin oxide, indium oxide, titanium oxide, silicon oxide, aluminum oxide, or the like, as well as combinations of one or a plurality thereof. The dielectric material can also contain silicon nitride, silicon carbide, or aluminum nitride.

This layer structure is generally obtained by a sequence of deposition operations that are carried out by a vacuum method such as magnetic field enhanced cathodic sputtering. Very fine metal layers, which contain, in particular, titanium or niobium, can also be provided on both sides of the silver layer. The lower metal layer serves as an adhesion and crystallization layer. The upper metal layer serves as a protective and getter layer to prevent modification of the silver during the further process steps.

Particularly suitable transparent, electrically conductive coatings contain at least one metal, preferably silver, nickel, chromium, niobium, tin, titanium, copper, palladium, zinc, gold, cadmium, aluminum, silicon, tungsten, or alloys thereof, and/or at least one metal oxide layer, preferably tin-doped indium oxide (ITO), aluminum-doped zinc oxide (AZO), fluorine-doped tin oxide (FTO, $SnO_2$:F), antimony-doped tin oxide (ATO, $SnO_2$:Sb), and/or carbon nanotubes and/or optically transparent, electrically conductive polymers, preferably poly(3,4-ethylene dioxythiophenes), polystyrene sulfonate, poly(4,4-dioctyl-cylopentadithiophene), 2,3-dichloro-5,6-dicyano-1,4-benzoquinone, mixtures, and/or copolymers thereof.

The thickness of the transparent, electrically conductive coating can vary widely and be adapted to the requirements of the individual case. It is essential here that the thickness of the transparent, electrically conductive coating not be so great that it becomes nontransparent to electromagnetic radiation, preferably electromagnetic radiation of a wavelength from 300 nm to 1300 nm and in particular visible light from 390 nm to 780 nm. The transparent, electrically conductive coating preferably has a layer thickness of 10 nm to 5 μm and particularly preferably of 30 nm to 1 μm.

The sheet resistance of the transparent, electrically conductive coating is preferably from 0.35 ohm/square to 200 ohm/square, preferably 0.5 ohm/square to 200 ohm/square, most particularly preferably from 0.6 ohm/square to 30 ohm/square, and in particular from 2 ohm/square to 20 ohm/square. The transparent, electrically conductive coating can, in principle, have even lower sheet resistances than 0.35 ohm/square, in particular if, in the case of their use, only a low light transmittance is required. Such sheet resistances are particularly suitable for detecting damage to the electrically conductive coating in the event of breakage of the first pane. The transparent, electrically conductive coating preferably has good infrared reflection properties and/or particularly low emissivity (low-E).

In an advantageous embodiment of the alarm pane arrangement according to the invention, the capacitive sensor is implemented as an individual component, i.e., in the form of a structural unit. In particular for the case in which the capacitive sensor has precisely one measuring electrode, or (in particular precisely) one measuring electrode and (in particular precisely) one reference ground electrode, or (in particular precisely) one measuring electrode, (in particular precisely) one reference ground electrode and at least one compensation electrode, all electrodes are in each case a component of the individual component. The capacitive sensor can be surrounded, in particular by one same (e.g., opaque) housing, wherein the electrode(s) can be arranged inside the housing.

In an advantageous embodiment of the alarm pane arrangement according to the invention, the shape of a detection region of the capacitive sensor corresponds to the shape of the measuring electrode.

Another aspect of the invention includes a method for operating an alarm pane arrangement according to the invention, wherein the measurement of the measurement signal is done continuously or periodically, preferably with a period length of 0.2 s to 100 s and is output as an output signal by the sensor unit. The output of the output signal can be done continuously or periodically, preferably with a period length of 0.2 s to 100 s.

Another aspect of the invention includes the use of an alarm pane arrangement according to the invention as glazing of a display case, a showcase, preferably for the protection of valuable goods such as paintings, textiles, jewelry, for example, in a museum or at a jeweler's, or as architectural glazing, insulating glazing, double insulating glazing, triple insulating glazing, fire resistant glazing, safety glazing, or as glazing in a vehicle on land, on water, or in the air, such as a motor vehicle, a bus, a train, or an aircraft.

Another aspect of the invention includes a use of a sensor unit according to the invention with a capacitive sensor for retrofitting a glazing with a first pane of toughened glass and a transparent, electrically conductive coating on the inside surface (II) to form an alarm pane arrangement.

Figure 1B:
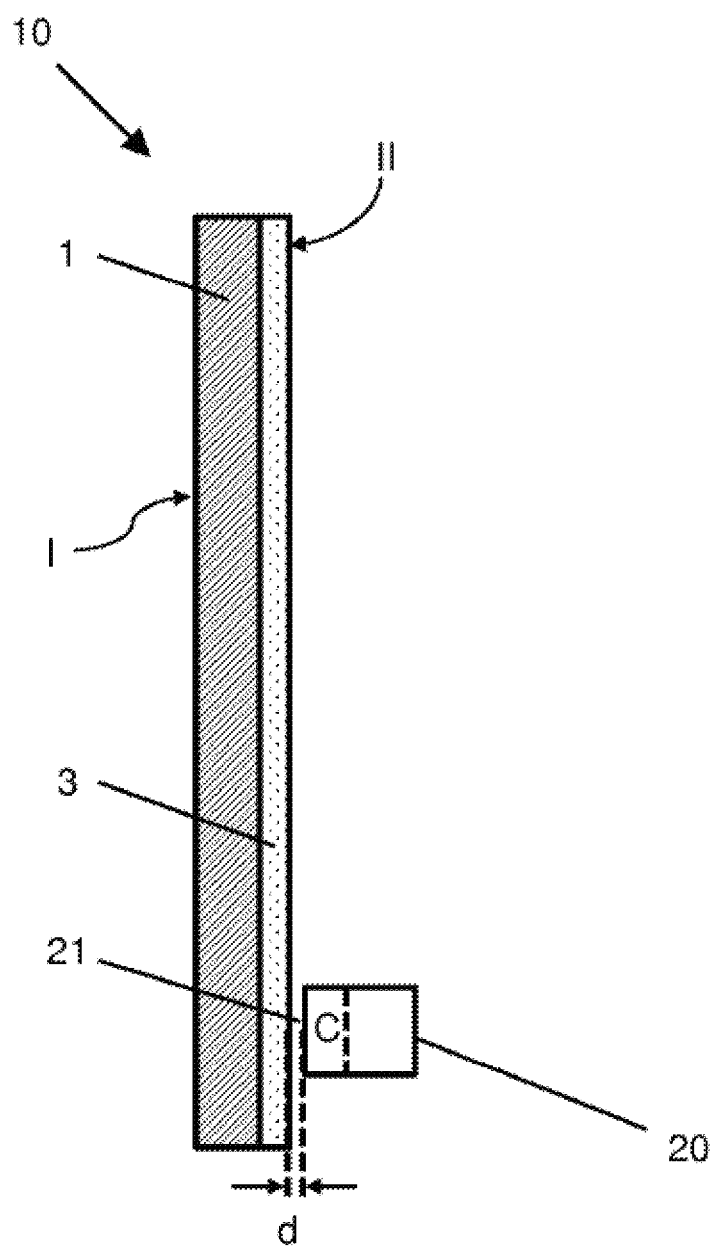
Figure 2A:
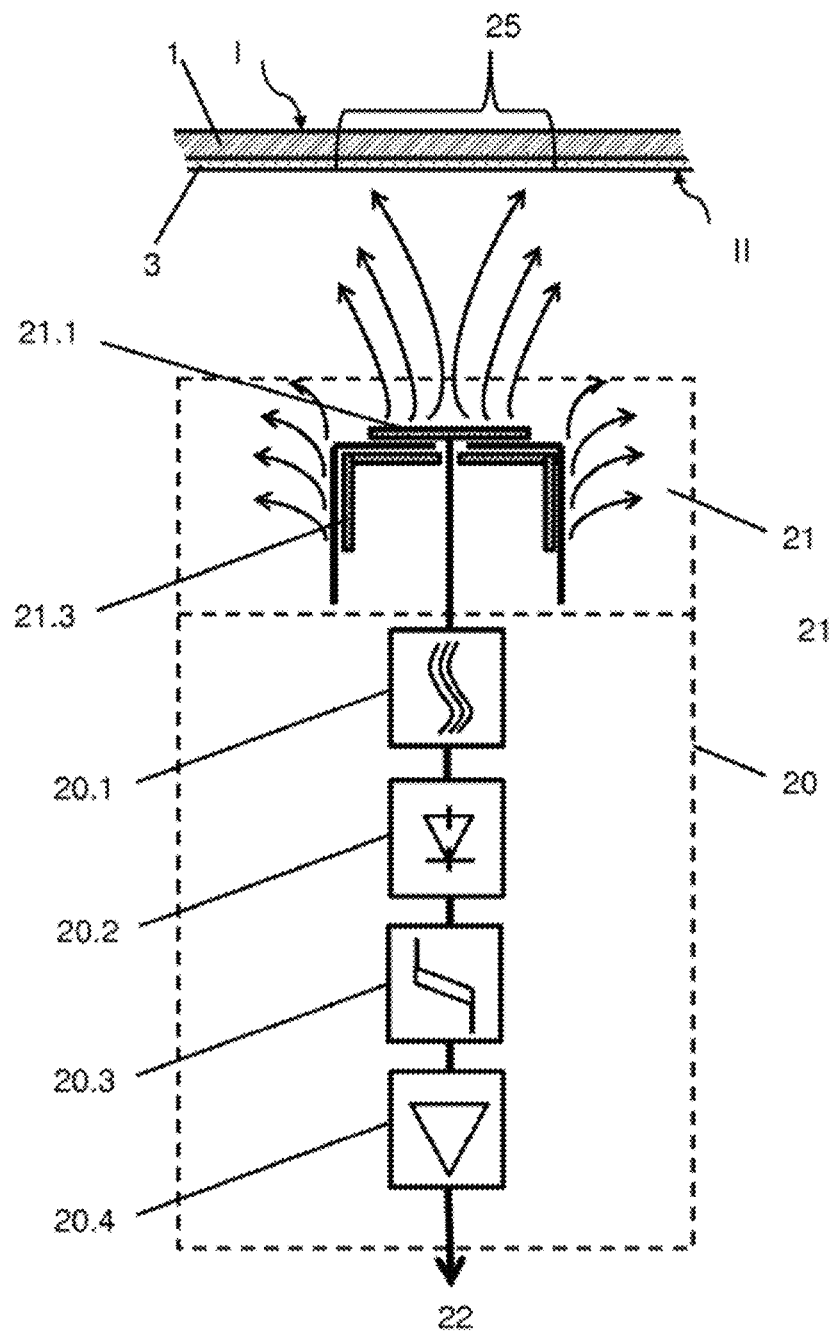
Figure 2B:
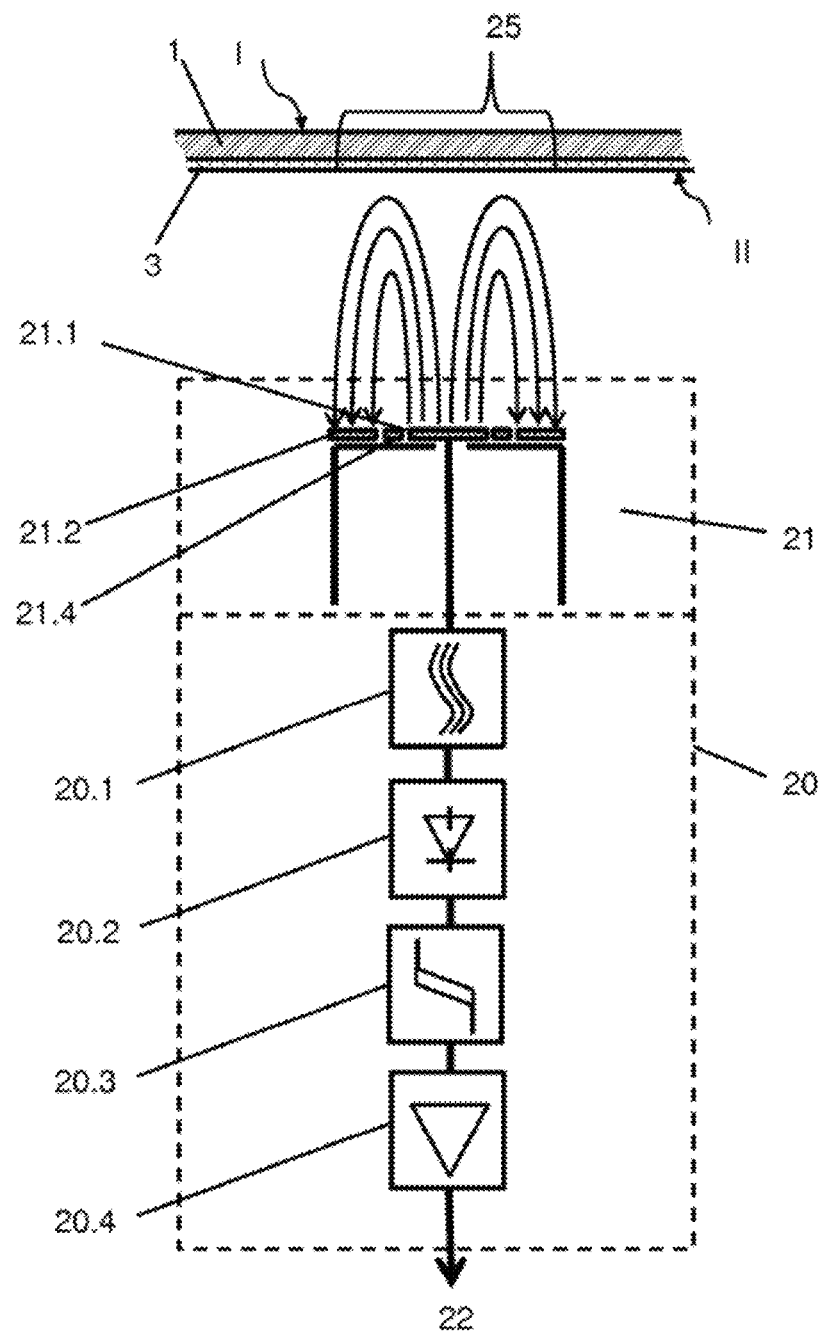
Figure 3A:
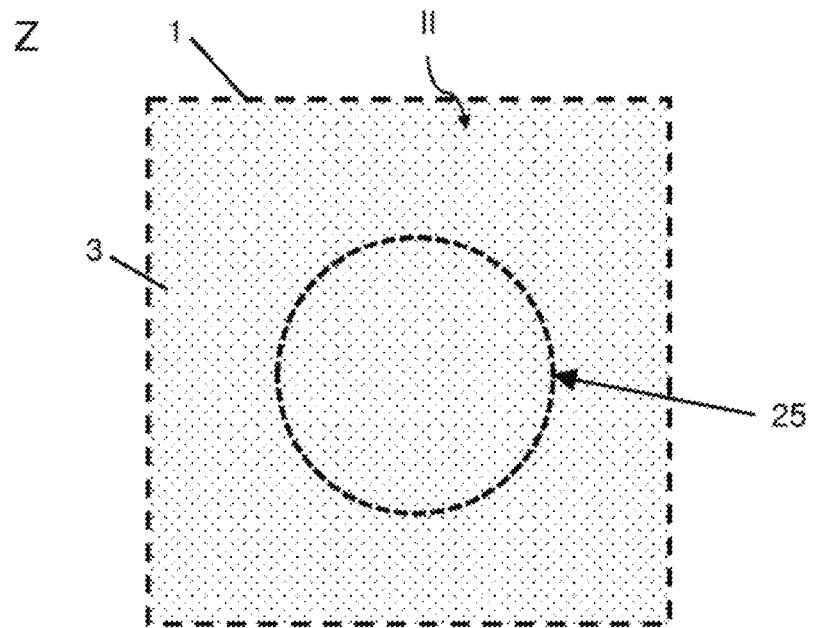
Figure 3B:
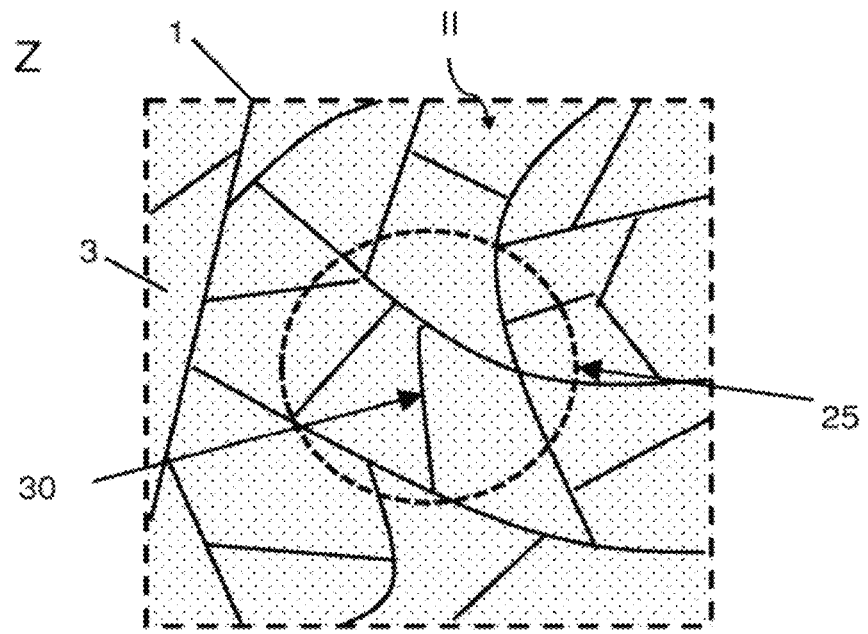
Figure 4A:
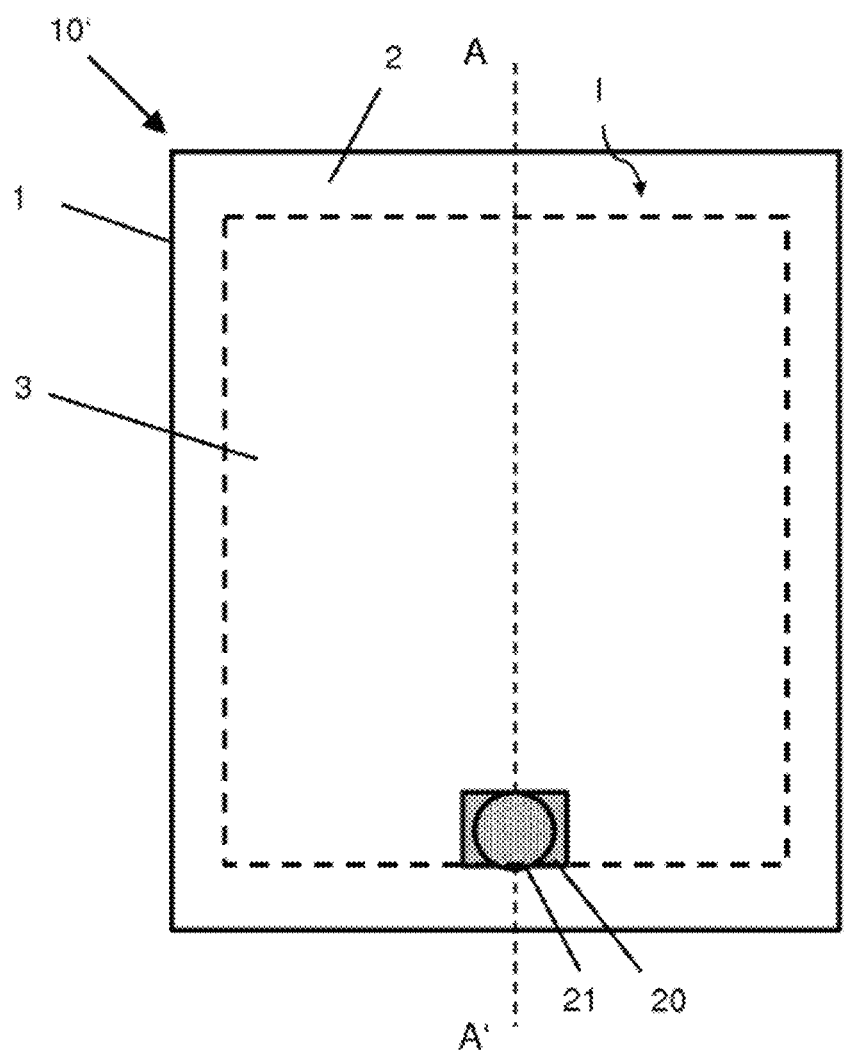
Figure 4B:
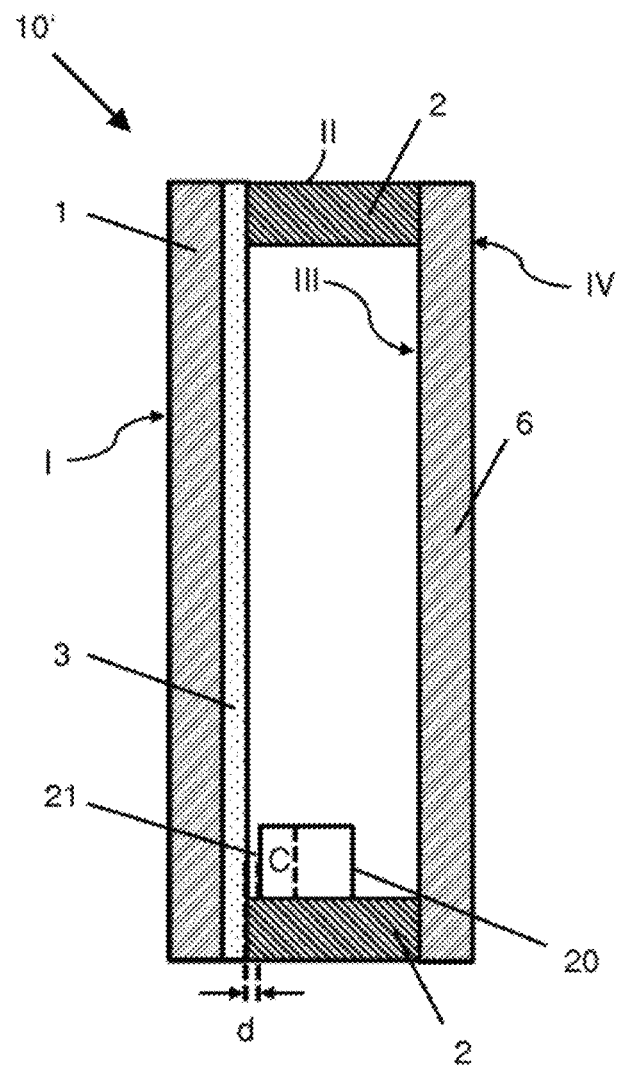

In the following, the invention is explained in detail with reference to drawings and an example. The drawings are not entirely to scale. The invention is in no way restricted by the drawings. They depict:

FIG. 1A a schematic view of an alarm pane arrangement according to the invention in a plan view, FIG. 1B a cross-sectional view along the section line A-A' of FIG. 1A, FIG. 2A a schematic view of a sensor unit according to the invention, FIG. 2B a schematic view of an alternative sensor unit according to the invention, FIG. 3A an enlarged view of the detail Z of the transparent, electrically conductive coating according to the invention with an undamaged first pane, FIG. 3B an enlarged view of the detail Z of the transparent, electrically conductive coating according to the invention with a broken first pane, FIG. 4A a schematic view of an alternative alarm pane arrangement according to the invention in a plan view, and FIG. 4B a cross-sectional view along the section line A-A' of FIG. 4A.

FIG. 1A depicts a schematic view of an alarm pane arrangement 10 according to the invention in a plan view of the outside surface I. FIG. 1B depicts a cross-sectional view along the section line A-A' of FIG. 1A.

The alarm pane arrangement 10 separates an interior from an exterior environment. The alarm pane arrangement 10 is, for example, suitable for protecting valuable items in the interior, for example, in a display case, in a museum, or at a jeweler's against outside access.

The alarm pane arrangement 10 comprises a first pane 1 on whose inside surface II a transparent, electrically conductive coating 3 is arranged. In this example, the transparent, electrically conductive coating 3 is arranged on the entire inside surface II of the first pane 1, minus an edge decoating with a width of, for example, 10 mm from the pane edge of the first pane 1. The edge decoating serves for corrosion protection against penetrating moisture via the pane edge.

The transparent, electrically conductive coating 3 serves, for example, as an infrared reflecting layer. This means that the share of thermal radiation from entering sunlight is largely reflected. With use of the first pane 1 in an architectural glazing, this provides for reduced heating of the interior by solar irradiation. The transparent, electrically conductive coating 3 is, for example, known from EP 0 847 965 B1 and includes two silver layers which are, in each case, embedded between multiple metal and metal oxide layers. The transparent, electrically conductive coating 3 has a sheet resistance of approx. 4 ohm/square.

The first pane 1 is, for example, a toughened soda lime glass pane with a width of 1 m, a length of 1.5 m, and a thickness of 4 mm. The first pane 1 is toughened, per DIN 12150-1 with a surface compressive stress of, for example, 120 N/mm$^2$. Due to the toughening, the first pane shatters upon damage into blunt-edged fragments with sizes of less 1 cm$^2$.

In the example depicted, a sensor unit 20 is arranged on the interior side of the first pane 1. Here, the "interior side" means the region that is turned toward the inside surface II, on which the transparent, electrically conductive coating 3 is arranged. The sensor unit 20 has a capacitive sensor 21 that is capacitively coupled to the electrically conductive coating 3. Of course, the capacitive sensor 21 need not necessarily be incorporated into the same housing as the rest of the sensor unit 20.

The distance d between the capacitive sensor 21 and the transparent, electrically conductive coating 3 is, for example, 0.5 mm. The capacitive sensor 21 and the transparent, electrically conductive coating 3 are, in particular, galvanically isolated from one another. The sensor unit measures, via the capacitive sensor 21, the capacitance of this arrangement and compares the measured value with a comparison value. The comparison value is specified with the undamaged first pane 1 with an undamaged transparent, electrically conductive coating 3. The sensor unit 20 determines the deviation, i.e., the difference of the measurement signal of the capacitive sensor 21 from the comparison value and outputs an alarm signal in the event of deviations that are greater than a defined tolerance. The alarm signal is, for example, a voltage or a voltage pulse with a specific level and/or pulse duration that differs from another neutral output signal, by which means an alarm condition can be identified. Such a deviation typically results upon breakage of the first pane 1 and damage to the transparent, electrically conductive coating 3 associated therewith.

The alarm signal is, for example, forwarded via a transmitter unit to a receiver to be converted there into an acoustic signal or to send an emergency call.

FIG. 2A depicts a schematic view of a sensor unit 20 according to the invention. The sensor unit 20 has a capacitive sensor 21. The capacitive sensor 21 includes a measuring electrode 21.1, which is connected to an electronic system via a lead. In addition, the capacitive sensor 21 includes, for example, a shield electrode 21.3 for the bundling of the capacitive field. Here, the capacitive sensor 21 is, for example, implemented without an explicit ground electrode, in other words, the reference ground electrode is not integrated into the capacitive sensor 21, but is represented by the object to be detected, i.e., by the transparent electrically conductive coating 3.

The sensor unit 20 has, for example, a plurality of structural stages: the measuring electrode 21.1 of the capacitive sensor 21 is connected to an oscillator 20.1. The oscillator 20.1 is connected to a comparator 20.3 via a demodulator 20.2. The comparator 20.3 compares the measurement signal with a comparison value and, as appropriate, outputs an alarm signal via the power amplifier 20.4 on the output 22.

The detection region 25, in which the changes in the transparent, electrically conductive coating 3 can be measured particularly precisely, is defined by the design of the capacitive sensor 21 and the distance between the capacitive sensor 21 and the transparent, electrically conductive coating 3. The measuring electrode 21.1 has, for example, the form of a circular pane such that a circular-pane-shaped detection region 25 results.

FIG. 2B depicts a schematic view of an alternative sensor unit 20 according to the invention, as it is used, for example, in the above referenced exemplary embodiment according to FIGS. 1A and 1B. The sensor unit 20 as a capacitive sensor 21. The capacitive sensor 21 includes a measuring electrode 21.1, which is connected to an electronics system via a lead. In addition, the capacitive sensor 21 includes a reference ground electrode 21.2, which is arranged in the form of a ring around the measuring electrode 21.1, here, for example, circular pane shaped. A compensation electrode 21.4, for example, is arranged between the measuring electrode 21.1 and the reference ground electrode 21.2. The compensation electrode 21.4 reduces measurement errors, which can result, for example, from moisture deposits on the measurement area consisting of the measuring electrode 21.1 and the reference ground electrode 21.2. Such capacitive sensors 21 are particularly suitable for measurement with transparent, electrically conductive coatings 3 with a high sheet resistance.

The sensor unit 20 has, for example, a plurality of structural stages: the measuring electrode 21.1 and reference ground electrode 21.2 of the capacitive sensor 21 are connected to an oscillator 20.1. The oscillator 20.1 is connected to a comparator 20.3 via a demodulator 20.2. The comparator 20.3 compares the measurement signal with a comparison value and, as appropriate, outputs an alarm signal to the output 22 via the power amplifier 20.4.

The detection region 25, in which the changes in the transparent, electrically conductive coating 3 can be measured particularly precisely, is defined by the design of the capacitive sensor 21 and the distance between the capacitive sensor 21 and the transparent, electrically conductive coating 3. The measuring electrode 21.1 has, for example, the shape of a circular pane such that a circular-pane-shaped detection region 25 results.

FIG. 3A depicts an enlarged view of the detail Z of the transparent, electrically conductive coating 3 according to the invention with an undamaged first pane 1. The transparent, electrically conductive coating 3 is undamaged in particular in the detection region 25 of the capacitive sensor 21.

FIG. 3B depicts an enlarged view of the detail Z of the transparent, electrically conductive coating 3 with a broken first pane 1. By means of damage, for example, due to the attempt to penetrate through the first pane 1, this has shattered into small fragments because of its toughening. This results in interruption of the transparent, electrically conductive coating 3 by break lines 30. The fragments are, in each case, smaller than the detection region 25 such that at least one break line 30 is arranged in the detection region 25. By means of the interruption of the transparent, electrically conductive coating 3 by break lines 30, the measurement signal of the capacitive sensor 21 changes and an alarm signal can be output.

FIG. 4A depicts a schematic view of an alternative alarm pane arrangement 10' according to the invention in plan view; and FIG. 4B, a cross-sectional view along the section line A-A' of FIG. 4A. The alarm pane arrangement 10' is, for example, an insulating glass pane, which includes the alarm pane arrangement 10 of FIGS. 1A and 1B. Additionally, the first pane 1 is bonded to a second pane 6 via a circumferential spacer 2. Here, the sensor unit 20 with a capacitive sensor 21 is arranged in the intermediate space that is formed by the first pane 1, the second pane 6, and the spacer 2. The sensor unit 20 is, for example, adhesively bonded on the lower section of the spacer 2 and thus securely fastened against slippage. The sensor unit 20 includes, for example, an accumulator and a solar cell, which charges the accumulator. Furthermore, the sensor unit 20 includes, for example, a transmitter unit that transmits an alarm signal via a Bluetooth connection to a receiver (not shown here) arranged outside the alarm pane arrangement 10'. The sensor unit 20 is energy self-sufficient and requires no leads outward—either for the energy supply, or for forwarding an alarm signal. The sensor unit 20 can, for example, be retrofitted in a simple manner into an already existing insulating glass unit.

This result was unexpected and surprising for the person skilled in the art.

LIST OF REFERENCE CHARACTERS

1 first pane
2 spacer
3 transparent, electrically conductive coating
6 second pane
10,10' alarm pane arrangement
20 sensor unit
20.1 oscillator
20.2 demodulator
20.3 comparator
20.4 power amplifier
21 capacitive sensor
21.1 measuring electrode
21.2 reference ground electrode
21.3 shield electrode
21.4 compensation electrode
22 output
25 detection region
30 break line
A-A' section line
C capacitance
Z detail
I outside surface of the first pane 1
II inside surface of the first pane 1
III outside surface of the second pane 6
IV inside surface of the second pane 6

The invention claimed is:

1. An alarm pane arrangement, comprising:
a first pane, made of toughened glass and with an effective relative permittivity number $\varepsilon_{eff}$ of 6 to 8, having an outside surface and an inside surface,
a transparent, electrically conductive coating having a sheet resistance of 0.35 ohm/square to 200 ohm/square, arranged on the inside surface of the first pane,
a sensor unit device with a capacitive sensor, coupled to the transparent, electrically conductive coating, wherein the sensor unit device outputs an alarm signal in an event of deviations in a measurement signal of the capacitive sensor from a comparison value,
wherein the first pane is toughened such that in an event of breakage of the first pane, fragments from the first pane are smaller than a detection region of the capacitive sensor,
wherein the capacitive sensor comprises one of:
i) a measuring electrode or
ii) a measuring electrode and a reference ground electrode or
iii) a measuring electrode, a reference ground electrode, and a compensation electrode, and
wherein the measuring electrode is galvanically isolated from the transparent, electrically conductive coating.

2. The alarm pane arrangement according to claim 1, wherein the transparent, electrically conductive coating is bonded to the first pane such that in an event of breakage of the first pane, the transparent, electrically conductive coating is damaged.

3. The alarm pane arrangement according to claim 2, wherein the transparent, electrically conductive coating is deposited directly on the inside surface of the first pane.

4. The alarm pane arrangement according to claim 3, wherein the transparent, electrically conductive coating is deposited as a thin-film stack.

5. The alarm pane arrangement according to claim 1, wherein a distance between the measuring electrode and the transparent, electrically conductive coating is from 0.1 mm to 20 mm.

6. The alarm pane arrangement according to claim 1, wherein the sensor unit device comprises a transmitter unit.

7. The alarm pane arrangement according to claim 6, wherein the transmitter unit comprises a radio transmitter unit.

8. The alarm pane arrangement according to claim 6, wherein the transmitter unit comprises at least one of a) Bluetooth, b) WLAN, or c) infrared transmitter.

9. The alarm pane arrangement according to claim 1, wherein the sensor unit device comprises an energy supply.

10. The alarm pane arrangement according to claim 9, wherein the energy supply includes at least one of: a battery, an accumulator, a supercapacitor, a thermoelectric generator, and a solar cell.

11. The alarm pane arrangement according to claim 9, wherein the sensor unit device does not have leads to an external power supply.

12. The alarm pane arrangement according to claim 1, wherein the first pane is connected to a second pane via a spacer.

13. The alarm pane arrangement according to claim 12, wherein the sensor unit device is arranged in an intermediate space between the first pane and the second pane.

14. The alarm pane arrangement according to claim 12, wherein the spacer is a circumferential spacer completely surrounding an edge of the first pane.

15. The alarm pane arrangement according to claim 1, wherein the first pane comprises at least one of: flat glass, float glass, quartz glass, borosilicate glass, and soda lime glass.

16. The alarm pane arrangement according to claim 1, wherein the transparent, electrically conductive coating comprises at least one of: a metal, a metal oxide layer, carbon nanotubes, optically transparent, and electrically conductive polymers.

17. The alarm pane arrangement according to claim 16, wherein the metal is silver.

18. The alarm pane arrangement according to claim 1, wherein the transparent, electrically conductive coating is arranged on at least 50% of an area of an inside surface of the first pane.

19. The alarm pane arrangement according to claim 1, wherein the capacitive sensor is implemented as an individual component.

20. The alarm pane arrangement according to claim 1, wherein a shape of a detection region of the capacitive sensor and a shape of the measuring electrode correspond to one another.

21. A method for operating an alarm pane arrangement, comprising:
    providing an alarm pane arrangement according to claim 1,
    measuring the measurement signal continuously or periodically to generate a measurement, and
    outputting the measurement as an output signal from the sensor unit device.

22. A method of using an alarm pane arrangement, comprising:
    providing an alarm pane arrangement according to claim 1, and
    using the alarm pane arrangement as glazing of a display case or a showcase.

23. The alarm pane arrangement according to claim 1, wherein a distance between the measuring electrode and the transparent, electrically conductive coating is from 0.2 mm to 10 mm.

24. The alarm pane arrangement according to claim 1, wherein the transparent, electrically conductive coating is arranged on at least 70% of an area of the inside surface of the first pane.

* * * * *